US011975216B2

(12) United States Patent
Zhao et al.

(10) Patent No.: US 11,975,216 B2
(45) Date of Patent: May 7, 2024

(54) RADIATION TREATMENT HEAD AND RADIATION TREATMENT DEVICE

(71) Applicant: OUR UNITED CORPORATION, Xi'an (CN)

(72) Inventors: Hongbin Zhao, Xi'an (CN); Huiliang Wang, Xi'an (CN); Ming Zhong, Xi'an (CN); Haifeng Liu, Xi'an (CN)

(73) Assignee: Our United Corporation, Xi'an (CN)

( * ) Notice: Subject to any disclaimer, the term of this patent is extended or adjusted under 35 U.S.C. 154(b) by 835 days.

(21) Appl. No.: 17/046,664

(22) PCT Filed: Apr. 26, 2018

(86) PCT No.: PCT/CN2018/084547
§ 371 (c)(1),
(2) Date: Oct. 9, 2020

(87) PCT Pub. No.: WO2019/196137
PCT Pub. Date: Oct. 17, 2019

(65) Prior Publication Data
US 2021/0031053 A1 Feb. 4, 2021

(30) Foreign Application Priority Data

Apr. 9, 2018 (CN) .......................... 201810309948.3

(51) Int. Cl.
*A61N 5/10* (2006.01)
(52) U.S. Cl.
CPC ......... *A61N 5/1031* (2013.01); *A61N 5/1045* (2013.01); *A61N 5/1077* (2013.01)
(58) Field of Classification Search
None
See application file for complete search history.

(56) References Cited

U.S. PATENT DOCUMENTS 5,627,870 A * 5/1997 Kopecky .............. A61N 5/1084
378/68
2004/0184577 A1* 9/2004 Carlsson .................. G21K 1/04
378/65
(Continued)

FOREIGN PATENT DOCUMENTS

CN 102256434 A 11/2011
CN 103285526 A 9/2013
(Continued)

OTHER PUBLICATIONS

International Search Report and Written Opinion of corresponding PCT Application PCT/CN2018/084547—18 pages (dated Jan. 11, 2019).

(Continued)

*Primary Examiner* — Marcus H Taningco
(74) *Attorney, Agent, or Firm* — Knobbe, Martens, Olson & Bear, LLP

(57) ABSTRACT

A radiation treatment head can include: a radiation source and a primary collimator, wherein the radiation source is configured to emit a radioactive beam; wherein the primary collimator is provided with a plurality of primary collimation channel groups; each of the primary collimation channel groups includes at least one primary collimation channel; and the radiation source and the primary collimator are movable relative to each other, so that the beam emitted from the radiation source is permissible to pass through any one of the primary collimation channels; and wherein the beam emitted from the radiation source, after passing through primary collimation channels of different primary collimation channel groups, forms fields with different sizes of areas on a reference plane.

18 Claims, 5 Drawing Sheets

(56) References Cited

U.S. PATENT DOCUMENTS

| | | | | |
|---|---|---|---|---|
| 2011/0317895 A1* | 12/2011 | Poludniowski | ...... | A61N 5/1049 378/4 |
| 2013/0221243 A1 | 8/2013 | Perkins | | |
| 2015/0202465 A1* | 7/2015 | Zhao | ........................ | A61N 5/06 600/1 |
| 2018/0318607 A1* | 11/2018 | Wilbur | ................... | G01B 11/27 |
| 2019/0001146 A1* | 1/2019 | Liu | .......................... | A61N 5/01 |

FOREIGN PATENT DOCUMENTS

| | | | |
|---|---|---|---|
| CN | 104658629 | A | 5/2015 |
| CN | 106075745 | A | 11/2016 |
| CN | 106456991 | A | 2/2017 |
| CN | 107456663 | A | 12/2017 |
| CN | 107485801 | A | 12/2017 |
| CN | 208678191 | U | 4/2019 |
| JP | 2-237577 | A | 9/1990 |

OTHER PUBLICATIONS

First Office Action of corresponding Chinese Application No. 201810309948.3—16 pages (dated Mar. 5, 2019).

Second Office Action of corresponding Chinese application No. 201810309948.3—10 pages (dated May 29, 2019).

Notification to Grant Patent Right for Invention of corresponding Chinese application No. 201810309948.3—6 pages (dated Sep. 4, 2019).

Biggs, "Analysis of Field and Custom Block Sizes Used in Radiation Therapy—Implications for Multileaf Collimator Design", Medical Dosimetry vol. 16—4 pages (1991).

Magliari MS, CMD, "IMRT and VMAT: Current and Future Best Practices"—51 pages.

Magliari MS, CMD, "IMRT and VMAT: Current and Future Best Practices"—51 pages (Jun. 29, 2017).

* cited by examiner

RADIATION TREATMENT HEAD AND RADIATION TREATMENT DEVICE

INCORPORATION BY REFERENCE TO ANY PRIORITY APPLICATIONS

The present disclosure is a national phase application of PCT International Application No. PCT/CN2018/084547, filed on Apr. 26, 2018, which claims priority to Chinese Patent Application No. 201810309948.3, filed on Apr. 9, 2018 and entitled "RADIO-THERAPEUTIC HEAD AND RADIO-THERAPEUTIC EVICE", the contents of which are incorporated herein by reference in their entireties.

TECHNICAL FIELD

The present disclosure relates to the field of medical technologies, and in particular relates to a radiation treatment head and a radiation treatment device.

BACKGROUND

Generally, an accelerator includes an electron gun, a bremsstrahlung target and a guiding device. The electron gun is configured to accelerate electrons to a relativistic velocity and guide the electron beam formed therefrom to hit the bremsstrahlung target to generate an X beam. The guiding device is configured to guide the X beam to form a beam that meets specific needs.

SUMMARY

The present disclosure provides a radiation treatment head and a radiation treatment device.

In one aspect, embodiments of the present disclosure provide a radiation treatment head including a radiation source and a primary collimator, wherein the radiation source is configured to emit a radioactive beam;

wherein the primary collimator is provided with a plurality of primary collimation channel groups; each of the primary collimation channel groups includes at least one primary collimation channel; and the radiation source and the primary collimator are movable relative to each other, so that the beam emitted from the radiation source is permissible to pass through any one of the primary collimation channels; and wherein the beam emitted from the radiation source, after passing through primary collimation channels of different primary collimation channel groups, forms fields with different sizes of areas on a reference plane.

Optionally, the beam emitted from the radiation source, after passing through the respective primary collimation channels in a same primary collimation channel group, forms fields with different characteristic parameters on the reference plane, wherein the characteristic parameters include a dose rate parameter and a penumbra parameter of a field.

Optionally, each of the primary collimation channel group includes at least two primary collimation channels, in which at least one is provided with a flattening filter, so that the beam, after passing through the at least two primary collimation channels, forms fields with different characteristic parameters of fields on the reference plane.

Optionally, no flattening filter is provided in one of the primary collimation channels in a primary collimation channel group.

Optionally, the radiation treatment head further includes a secondary collimator assembly, wherein the secondary collimator assembly includes a multi-leaf collimator MLC, and the MLC includes a plurality of leaves in opposite arrangement and movable relative to each other; and wherein a length p of the leaf of the MLC satisfies the following formula:

$$\frac{d_1}{2} \cdot \frac{h_1}{h_2} \leq p < d_2 \cdot \frac{h_1}{h_2},$$

where $h_1$ represents a distance between the radiation source and the leaf, $h_2$ represents a distance between the radiation source and the reference plane, $d_1$ represents a minimum length, in a movement direction of the leaf, of a field formed on the reference plane by the beam passing through primary collimation channels after being emitted from the radiation source, and $d_2$ represents a maximum length, in a movement direction of the leaf, of a field formed on the reference plane by the beam passing through primary collimation channels after being emitted from the radiation source.

Optionally, the secondary collimator assembly further includes one or two diaphragms; and wherein when the secondary collimator assembly includes two diaphragms, a movement direction of a first one of the two diaphragms intersects a movement direction of a second one of the two diaphragms.

Optionally, the primary collimator is in a circular shape, and the plurality of primary collimation channels in the primary collimator are distributed in a circumferential array; and wherein the radiation source and the primary collimator are rotatable relative to each other, so that the beam emitted from the radiation source is permissible to pass through any one of the primary collimation channels.

Optionally, the primary collimator is plate-shaped, and the plurality of primary collimation channels in the primary collimator are distributed in a straight line or in an array.

Optionally, among the fields formed on the reference plane by the beam passing through the primary collimation channels after being emitted from the radiation source, a maximum file area is 40*40 $cm^2$, and a minimum file area is 28*28 $cm^2$; or among the fields formed on the reference plane by the beam passing through the primary collimation channels after being emitted from the radiation source, a maximum file area is 35*35 $cm^2$, and a minimum file area is 22*22 $cm^2$.

In another aspect, embodiments of the present disclosure provide a radiation treatment device including any one of the above-mentioned radiation treatment heads.

BRIEF DESCRIPTION OF DRAWINGS

In order to describe the technical solutions in the embodiments of the present disclosure more clearly, the following briefly introduces the accompanying drawings required for describing the embodiments. Apparently, the accompanying drawings in the following description show merely some embodiments of the present disclosure, and persons of ordinary skilled in the art may also derive other drawings from these accompanying drawings without creative efforts.

DESCRIPTION OF EMBODIMENTS

For clearer descriptions of the objects, technical solutions, and advantages of the present disclosure, the embodiments of the present disclosure are further described in detail in combination with the accompanying drawings.

In the medical technology industry, tumors are usually treated by a radiation treatment device. A radiation treatment head in the radiation treatment device typically includes a radiation source and a primary collimator. During the radiotherapy, a tumor focus area is required to match the focus of the radiation treatment head (that is, the isocenter of the radiation treatment device), so that tumor cells in the tumor focus area can be killed after the rays emitted from the radiation source, followed by passing through and being shaped by the primary collimator, are irradiated to the tumor focus area. The field formed by the radiation source and the dose rate at the focus are both in relation with the primary collimation channel of the primary collimator: if the primary collimation channel of the primary collimator is large, the field formed therefrom is large and the dose rate at the focus is low; and if the primary collimation channel of the primary collimator is small, the field formed therefrom is small and the dose rate at the focus is high. Here, the field of the radiation source can be a maximum irradiation range formed by the rays emitted from the radiation source on a reference plane (for example, a horizontal plane where the isocenter of the radiation treatment device is located). Generally, the primary collimation channels in the primary collimator have the same size and only form one type of field, resulting in poor flexibility of the radiation treatment head.

Figure 1A:
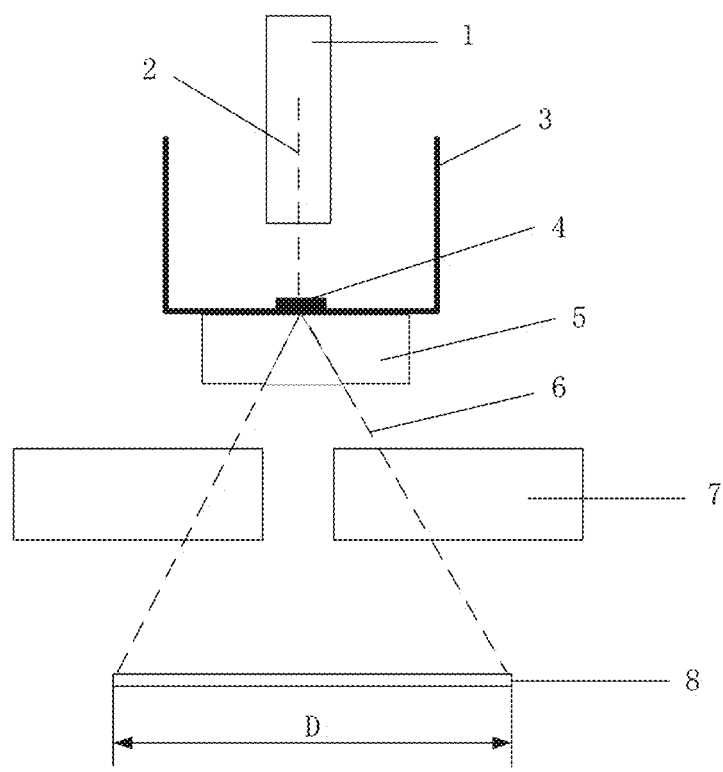
FIG. 1a is a schematic structural diagram of a radiation treatment head.

The accelerator is used for the radiation treatment of tumors. As shown in FIG. 1*a*, an electron gun 1 is enclosed in a vacuum chamber which has an outer wall 3, and an electron beam 2 is emitted from the electron gun 1 and hits a bremsstrahlung target 4, so that an X-ray beam is emitted. The X-ray beam then passes through a primary collimator 5, and is shaped into a cone-shaped beam 6 and then emitted out. Besides, during the radiotherapy, in order to make the beam match the shape of the tumor, an additional collimator device 7 can be provided for further shaping of the beam 6.

As the tumors to be treated have various sizes, for treating tumors of all sizes, the primary collimator 5 in the existing radiation treatment device shapes the X-ray beam into a relatively large cone-shaped beam 6, and its projection on a reference plane 8 is the field of D*D.

Figure 3:
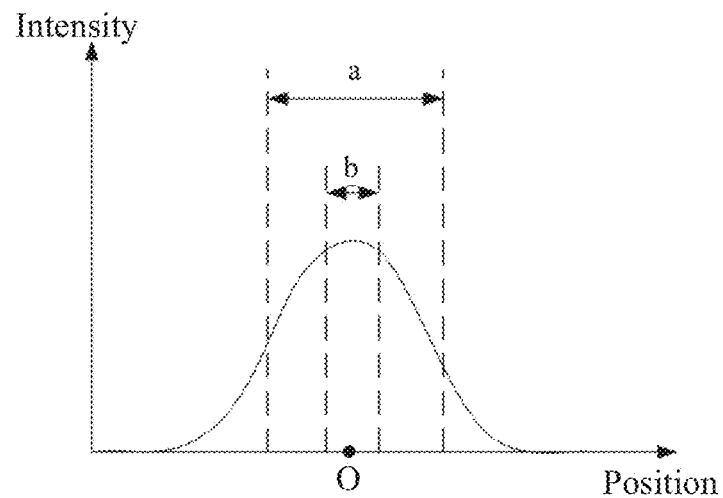
FIG. 3 is a diagram showing a relationship between an intensity of a ray and a position of the ray in a field according to an embodiment of the present disclosure.

Generally, the existing radiation treatment device generates a projected field of 40*40 cm$^2$. However, only about 5% of tumors require a field of this size for clinical radiotherapy. When treating 95% of smaller tumors with such a radiation treatment device, the following may occur. On one hand, the relatively large conical beam 6 formed by the primary collimator 5 may cause a radiation dose on the normal tissues surrounding the tumor. For reducing such radiation dose as much as possible, it is necessary to provide multiple secondary collimators (such as two multi-leaf gratings, two diaphragms, and the like) or a longer multi-leaf grating (such as the collimator device 7 in FIG. 1*a*). However, the former occupies the space of the beam light path, which in turn reduces the treatment space, and the latter results in a large rotation radius of the treatment head large and a multi-leaf grating with large mass, which impedes the improvement of movement characteristic of the leaves. On the other hand, as shown in FIG. 3, "a" indicates a field range required by a large tumor, and "b" indicates a field range required by a small tumor. In one example, about 50% of radiation dose in the middle portion (i.e., the portion subjected to high-intensity radiation) of a field is cut off by a flattening filter, so as to make the dose rate in the middle portion (the portion with high-intensity radiation) and that in the surrounding portion same. As such, in the case of treating small tumors, when a flattening filter is used, the effective available dose rate is further lowered, that is, the effective available dose rate for the small field is lowered.

However, embodiments of the present disclosure provide a radiation treatment head that can form different fields, and have higher flexibility.

Figure 1B:
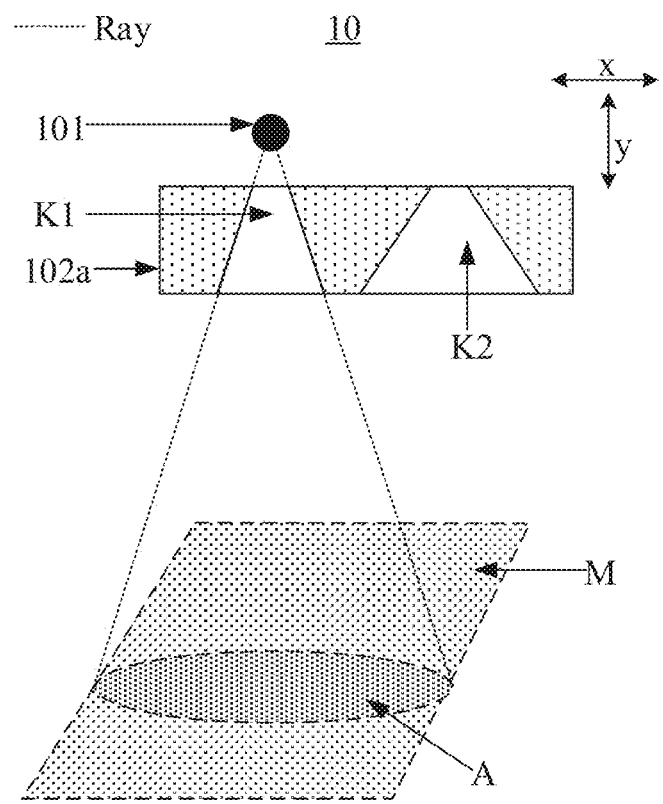
FIG. 1*b* is a schematic structural diagram of a radiation treatment head according to an embodiment of the present disclosure.

FIG. 1*b* is a schematic structural diagram of a radiation treatment head according to an embodiment of the present disclosure. As shown in FIG. 1*b*, the radiation treatment head 10 includes a radiation source 101 and a primary collimator 102*a*. The radiation source 101 is configured to emit a radioactive beam. The primary collimator is provided with a plurality of primary collimation channel groups (not marked in FIG. 1*b*), and each of the primary collimation channel groups includes at least one primary collimation channel. For example, a primary collimation channel K1 and a primary collimation channel K2 may belong to different primary collimation channel groups. The radiation source 101 and the primary collimator 102*a* are configured to be movable relative to each other, so that a beam emitted from the radiation source 101 can pass through any one of the primary collimation channels. When the beam emitted from the radiation source 101 passes through primary collimation channels of different primary collimation channel groups, the fields formed on a reference plane M have areas of different sizes.

It should be noted that the radiation source in the present disclosure may be an accelerator and the emitted beam may be an X-ray beam, or the radiation source may be an isotope radiation source (such as cobalt-60) and the emitted beam may be a γ-ray beam, or the radiation source may be a neutron or proton radiation source. This is not limited in the present disclosure, and for purpose of description, the accelerator is taken as an example of radiation source in the present disclosure. In addition, the radiation source 101 and the primary collimator 102*a* can be movable relative to each other in such a manner that the radiation source is fixed and the primary collimator is movable, or the primary collimator is fixed and the radiation source is movable, or both the radiation source and the primary collimator are movable, and the relative movement between them may be relative translation or relative rotation, etc., which is not limited in the present disclosure.

The beam emitted from the radiation source 101 may pass through the primary collimation channels of different primary collimation channel groups, and form fields with different sizes of areas on the reference plane M. For example, the primary collimator 102a may be a light-shielding plate structure, the primary collimation channels may all extend in a direction perpendicular to the plate structure(e.g., the y direction in FIG. 1b), and the radiation source 101 and the primary collimator 102a can move relative to each other in a direction parallel to the plate structure(e.g., the x direction in FIG. 1b), so that the radiation source 101 may directly face any one of the primary collimation channels and the beam emitted from the radiation source may pass through the primary collimation channel directly facing the radiation source. The primary collimation channel K1 and the primary collimation channel K2 may belong to different primary collimation channel groups. When the beam emitted from the radiation source 101 passes through the primary collimation channel K1 and forms a first field A on the reference plane M, and the beam emitted from the radiation source 101 passes through the primary collimation channel K2 and forms a second field on the reference plane M (not shown in FIG. 1b), the area of the first field is different from the area of the second field. The reference plane M may be located on a side, distal from the radiation source 101, of the primary collimator 102a and may be parallel to the x direction in FIG. 1b.

It should be noted that, the primary collimator in the radiation treatment head can shape the rays emitted from the radiation source, so that the rays can only pass through the primary collimation channel directly facing the radiation source and cannot pass through areas other than the primary collimation channel in the plate structure, thereby forming a desired field on the reference plane. FIG. 1b only illustrates the case that the primary collimator is provided with two primary collimation channel groups each including one primary collimation channel. In FIG. 1b, field A is illustrated as a circular field, and in this way, the primary collimation channel may be in a shape of truncated cone. In actual practice, the number of primary collimation channel groups may be three, four or more; the number of primary collimation channels included in each primary collimation channel group may be two, three or more; and the shape of the field may be square or rectangular, and the shape of the primary collimation channel may be in a shape of quadrangular pyramid frustum, which are not limited in the present disclosure. It should be further noted that the reference plane M in the present disclosure may be a set virtual plane, and the specific position thereof is not limited in the present disclosure. In practice, the reference plane may be a plane where a tumor center is located during the treatment of a patient.

In summary, the radiation treatment head provided by the embodiment of the present disclosure includes a radiation source and a primary collimator. The primary collimator is provided with a plurality of primary collimation channel groups, and each of the primary collimation channel groups includes at least one primary collimation channel, and the radiation source and the primary collimator are configured to be movable relative to each other, so that the beam emitted from the radiation source is permissible to pass through any one of the primary collimation channels; and the beam emitted from the radiation source, after passing through primary collimation channels of different primary collimation channel groups, can form fields with different sizes of areas on a reference plane. As such, the radiation source or the primary collimator can be moved to allow the beam emitted from the radiation source to pass through a primary collimation channel corresponding to a large field area when treating large tumors, and allow the beam emitted from the radiation source to pass through a primary collimation channel corresponding to a small field area when treating small tumors. Thus, a focus dose rate during the treatment of small tumors can be increased, and excess beams beyond the tumor treatment can be reduced. In this way, the radiation treatment head can form various fields, which improves the flexibility of the radiation treatment head.

It should be noted that in the following embodiments of the present disclosure, the case that the shape of the field is square is taken as an example (the existing detector plates are generally square). However, it can be understood that the shape of the field is not limited to square and may be in any other shape such as elliptical or circular. The illustrated shape is only an example for purpose of description in the present disclosure.

In an embodiment according to the present disclosure, after a beam is emitted from the radiation source and passes through respective primary collimation channels in a same primary collimation channel group, various fields formed by the beam on the reference plane may have different characteristic parameters. The field characteristic parameters may include, but are not limited to, a dose rate parameter and a penumbra parameter of a field. In an example implementation, each primary collimation channel group of the primary collimator may include at least two primary collimation channels, and at least one of the primary collimation channels in each primary collimation channel group may be provided with a flattening filter (FF). In another example embodiment, the primary collimation channel group may include a plurality of primary collimation channels, wherein two or more primary collimation channels may be respectively provided with FFs in different shapes, so that beams passing through different primary collimation channels are flattened to different degrees by the respective FFs, and thus the characteristic parameters of the fields formed on the reference plane are different. For example, in another implementation, no flattening filter is provided in one of the primary collimation channels in each primary collimation channel group, that is, the primary collimation channel is in a flattening filter-free (FFF) mode.

It should be noted that the FF may conduct an intensity adjustment on the rays emitted from the radiation source and make adjustment on the spatial distribution of the intensity of the rays, so that the intensity distribution of the rays after passing through the FF is uniform. For two same primary collimation channels, under the case that one channel has an FF and the other channel has no FF, after the beam emitted from the radiation source passes through the two channels, the field on the reference plane formed by the beams passing through the channel having the FF has a higher effective available dose rate than the field on the reference plane formed by the beams passing through the channel having no FF.

In the present disclosure, different FFs may be provided in different collimation channel groups. For example, a customized small flattening filter (SFF) may be provided in the primary collimation channel, so as to allow the beam passing through the primary collimation channel after being emitted from the radiation source to form a field on the reference plane with a relatively high dose rate and small field area. As described in the background part, when treating small tumors by using an FF mode, about 50% high-intensity radiation in the middle is cut off if an existing large field is applied; in contrast, only 20-30% high-intensity radiation in the middle needs to be cut off to flatten the intensity of the whole field if a small field according to the present disclosure is applied. Thus, in the present disclosure, the dose rate in the treatment for small tumors can be improved.

In the embodiment of the present disclosure, the FF is arranged within the primary collimation channel, so that the structure of the radiation treatment head is more compact, thereby reducing the volume of the radiation treatment head and increasing the accommodating space for a patient in the treatment. For example, in an embodiment of the present disclosure, the accommodating space for the patient may be in a column shape. The patient may lie on a substantially rectangular treatment couch during the treatment, and the length direction of the treatment couch may be the height direction of the column, and the diameter of the bottom surface of the column may be greater than 1 meter. In the example illustrated in FIG. 1a, the FF is arranged outside the primary collimation channel, which makes rays emitted from the radiation source be scattered when passing through the FF, and a shielding structure needs to be placed around the FF. In the embodiment of the present disclosure, even if the rays may be scattered when passing through the FF, as the scattered rays would be absorbed by the plate structure and no rays will be emitted out of the preset field, no additional shielding structure is required, thereby reducing the weight of the radiation treatment head.

Figure 2:
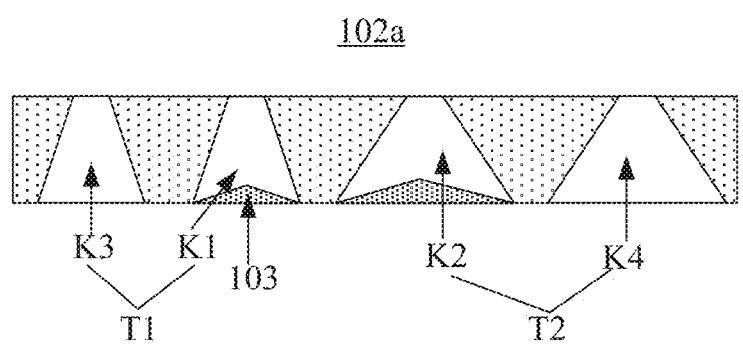
FIG. 2 is a schematic structural diagram of a primary collimator according to an embodiment of the present disclosure.

Optionally, FIG. 2 shows a schematic structural diagram of a primary collimator. On the basis of the primary collimator 102a in FIG. 1b, the primary collimator 102a in FIG. 2 includes a primary collimation channel group T1 and a primary collimation channel group T2. The primary collimation channel group T1 includes a primary collimation channel K1 and a primary collimation channel K3, and the primary collimation channel group T2 includes a primary collimation channel K2 and a primary collimation channel K4. Both K1 and K2 are provided with an FF 103, and both K3 and K4 are free of FF. After being emitted from the radiation source 101 and passing through the respective primary collimation channels in a same primary collimation channel group, the beam may form fields on the reference plane M which have the same field area but different characteristic parameters.

FIG. 3 shows a diagram illustrating a relationship between an intensity of a ray and positions of the ray in the field. For example, when the shape of the primary collimation channel through which the beam emitted from the radiation source passes is a truncated cone and the field formed on the reference plane is in a circular shape, in FIG. 3 illustrates the relationship with x-axis representing positions on a diameter of the field, the position O representing the center of the field, and y-axis representing the intensity of the ray at a certain position in the field (the unit may be gray per minute, i.e., Gy/Min). If the bottom surface, distal from the radiation source, of the primary collimation channel is large, the field formed on the reference plane by the radiation source directly facing the primary collimation channel will be relatively large in area (e.g., a field covering all the positions within the range indicated by "a"), and have a low ray intensity per unit area and a low effective available dose rate (i.e., the ray intensity in a unit area in the field). If the bottom surface of the primary collimation channel is small, the field formed on the reference plane by the radiation source directly facing the primary collimation channel will be relatively small in area (e.g., a field covering all the positions within the range indicated by "b"), and have a high ray intensity per unit area and a high effective available dose rate.

In a case as illustrated in FIG. 2, a field formed, by the beam emitted from the radiation source 101 and passing through the primary collimation channel K1, on the reference plane is a first field; a field formed, by the beam emitted from the radiation source 101 and passing through the primary collimation channel K2, on the reference plane is a second field; a field formed, by the beam emitted from the radiation source 101 and passing through the primary collimation channel K3, on the reference plane is a third field; a field formed, by the beam emitted from the radiation source 101 and passing through the primary collimation channel K4, on the reference plane is a fourth field; the bottom surface area of the primary collimation channel K2 is larger than that of the primary collimation channel K1, the bottom surface area of the primary collimation channel K1 is the same as that of the primary collimation channel K3, and the bottom surface area of the primary collimation channel K4 is the same as that of the primary collimation channel K2. Then the area of the second field may be greater than that of the first field, the area of the first field may be equal to that of the third field, and the area of the second field may be equal to that of the fourth field. For example, the areas of the first field and the third field may both be 28*28 cm$^2$, that is, both the first field and the third field may be a square with a side length of 28 cm; and the areas of the second field and the fourth field may both be 40*40 cm$^2$, that is, both the second field and the fourth field may be a square with a side length of 40 cm. The dose rate of the third field may be greater than that of the first field, the dose rate of the fourth field may be greater than that of the second field. Optionally, the areas of the first field and the third field may both be 22*22 cm$^2$, that is, both the first field and the third field may be a square with a side length of 22 cm; and the areas of the second field and the fourth field may both be 35*35 cm$^2$, that is, both the second field and the fourth field may be a square with a side length of 35 cm.

In a case, the radiation source emits an X-ray beam with an energy of 6 megavolts, when a tumor focus in the breast or prostate of a patient needs to be treated, a large field is required to be formed on the reference plane, and for this, primary collimation channel K2 or K4 can be used for allowing the beam emitted from the radiation source to pass through; when a tumor focus in the brain of a patient needs to be treated, or when a stereotactic body radiation therapy (SBRT) needs to be performed, a small field with a high effective available dose rate is required to be formed on the reference plane, and for this, the primary collimation channel K1 or K3 can be used for allowing the beam emitted from the radiation source to pass through.

It should be noted that, as the beam emitted from the radiation source, after passing through primary collimation channels of different primary collimation channel groups, forms fields with different sizes of areas on a reference plane, the radiation treatment head provided by the embodiment of the present disclosure can form various fields on the reference plane. In this way, even if different patients have different requirements on the field area and dose rate, the radiation treatment head provided in the embodiment of the present disclosure can still apply, without needing to change the radiation treatment heads. Also, the various fields may include a large field with a small dose rate, and a small field with a large dose rate.

Figure 4:
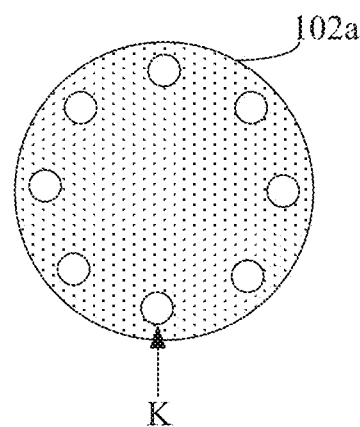
FIG. 4 is a schematic diagram of a primary collimator according to an embodiment of the present disclosure.

Optionally, FIG. 4 shows a schematic diagram of another primary collimator. The primary collimator 102a may be in a circular shape, and a plurality of primary collimation channels in the primary collimator may be distributed in a circumferential array. That is, the plurality of primary collimation channels K may be arranged in sequence around a center of the plate structure 102a, and each primary collimation channel K has a same distance to the center. The radiation source and the primary collimator are rotatable relative to each other, so that the beam emitted from the radiation source is permissible to pass through any one of the primary collimation channels. When it is necessary to change the primary collimation channel through which a beam emitted from the radiation source passes, the only operation needed may be to control the primary collimator to rotate by a certain angle around its center. Optionally, the primary collimator 102a may have a plate shape, such as a strip with a substantially rectangular shape.

The plurality of primary collimation channels in the primary collimator may be distributed in a straight line or in an array, that is, the plurality of primary collimation channels may be arranged in sequence along the length direction of the primary collimator 102a (i.e., the case illustrated in FIG. 2). When the primary collimation channel, through which the beam emitted from the radiation source passes, needs to be changed, it may be only necessary to control the primary collimator to move by a certain distance along its length direction. Optionally, the plurality of primary collimation channels may be arranged in several rows, and in each row, the primary collimation channels are arranged in sequence along the length of the primary collimator. In this case, when the primary collimation channel, through which the beam emitted from the radiation source passes, needs to be changed, may be is only necessary to control the primary collimator to move by a certain distance along its length direction and then move by a certain distance along its width direction.

In summary, the radiation treatment head provided by the embodiment of the present disclosure includes a radiation source and a primary collimator, wherein the primary collimator is provided with a plurality of primary collimation channel groups, and each of primary collimation channel groups includes at least one primary collimation channel; the radiation source and the primary collimator are configured to be movable relative to each other, so that a beam emitted from the radiation source is permissible to pass through any one of the primary collimation channels; and the beam emitted from the radiation source, after passing through primary collimation channels of different primary collimation channel groups, forms fields with different sizes of areas on a reference plane. In this way, the radiation treatment head can form various fields, which improves the flexibility of the radiation treatment head.

Figure 5:
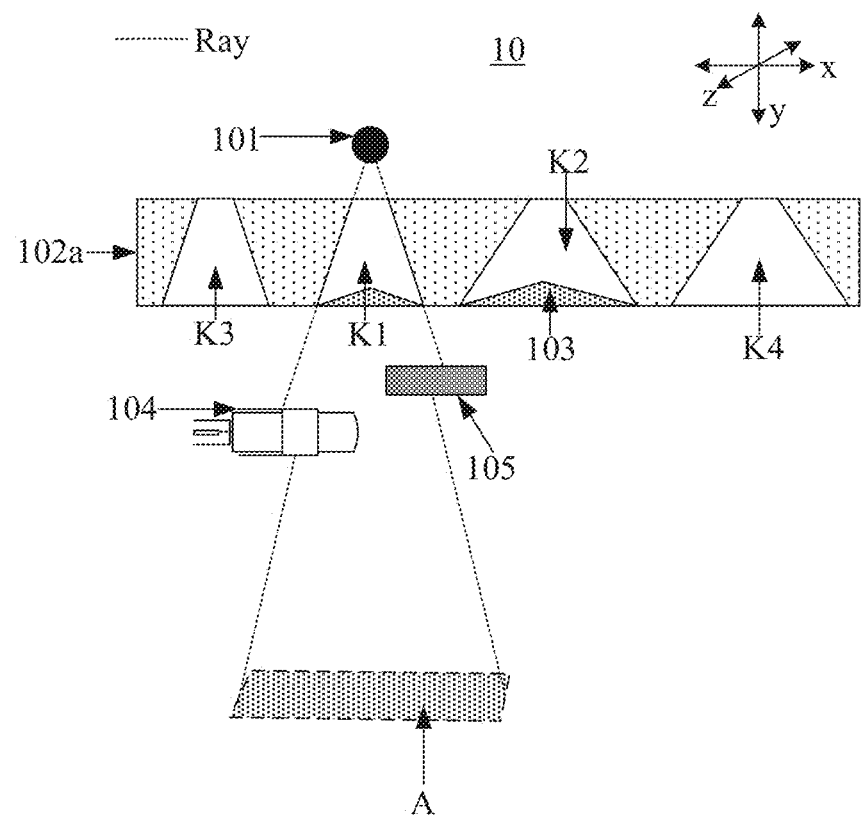
FIG. 5 is a schematic structural diagram of another radiation treatment head according to an embodiment of the present disclosure.

FIG. 5 is a schematic structural diagram of another radiation treatment head according to an embodiment of the present disclosure. On the basis of FIG. 1b, as shown in FIG. 5, the radiation treatment head may further include a secondary collimator assembly (not shown in FIG. 5), and the secondary collimator assembly may include a multi-leaf collimator (MLC) 104.

For example, the secondary collimator component may further include at least one of a first diaphragm 105 and a second diaphragm. FIG. 5 only illustrates the case that the secondary collimator assembly includes the first diaphragm 105. Optionally, when both the first diaphragm and the second diaphragm are included in the secondary collimator assembly, the two diaphragms may be arranged in sequence along the irradiating direction of the radiation source (e.g., the y direction in FIG. 5), and the movement direction of the first diaphragm intersects a movement direction of the second diaphragm. For example, the first diaphragm and the second diaphragm may be both located on a side, proximal to the radiation source, of the multi-leaf collimator; or both located on a side, distal from the radiation source, of the multi-leaf collimator; or one (i.e., an upper diaphragm) is located on the side, proximal to the radiation source, of the multi-leaf collimator, and the other (i.e., a lower diaphragm) is located on the side, distal from the radiation source, of the multi-leaf collimator. For example, the movement direction of the upper diaphragm may be x direction, the movement direction of the lower diaphragm may be z direction perpendicular to both x direction and y direction. The secondary collimator assembly may further include a wedge board (not shown in FIG. 5).

Figure 6:
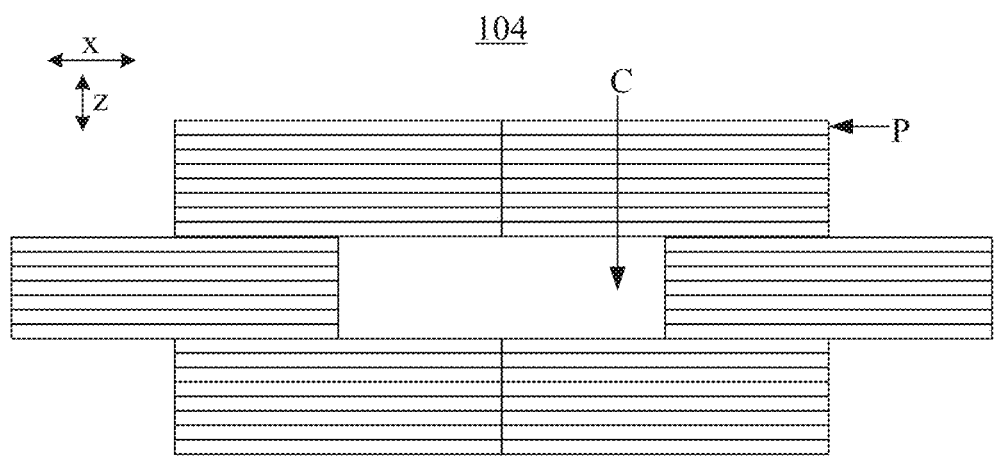
FIG. 6 is a schematic structural diagram of a multi-leaf collimator according to an embodiment of the present disclosure.

FIG. 6 is a schematic structural diagram of a multi-leaf collimator according to an embodiment of the present disclosure. The multi-leaf collimator 104 includes two sets of leaves opposite to each other in the x direction, wherein each leave set includes a plurality of leaves P tightly stacked along the z direction, and the thickness of the leaves ranges from 2 mm to 2.5 mm. It should be noted that each leaf may be in a rectangular shape, with z direction being the thickness direction of the leaf, x direction being the length direction of the leaf, and x direction being perpendicular to the z direction. Each leaf P can move along the length direction of the leaf (that is, the x direction shown in FIG. 6) under the control of a drive screw (not shown in the figure). The drive screw may control the two sets of leaves to define conformal regions with different shapes. As shown in FIG. 6, the conformal region C formed by the two sets of leaves has a rectangular shape. The plurality of leaves P can block the rays emitted by the radiation source from passing through, and the drive screw can control the two sets of leaves to enclose a conformal region which has a shape substantially the same as the shape of the patient focus.

Figure 7:
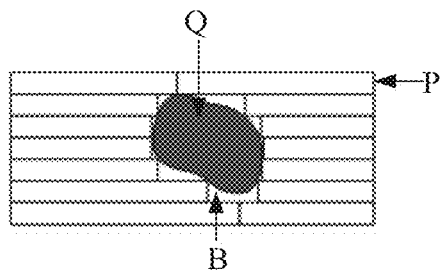
FIG. 7 is a schematic diagram of a multi-leaf collimator in an example.

FIG. 7 is a schematic diagram of a multi-leaf collimator in one example, and only partial structure of the leaves is shown. As illustrated in FIG. 7, Q may be a focus inside the patient, and the drive screw can control the two sets of leaves to define a conformal region B which has a shape substantially the same as that of the focus Q. In the example illustrated in FIG. 7, as the field formed by the primary collimator is large, a large multi-leaf collimator is also necessary. For example, if the length of leaves of the multi-leaf collimator is 20 cm (assuming that the leaves are located at the midpoint between the radiation source and the reference plane), the multi-leaf collimator may be capable of conforming to a field with a maximum area of 40*40 $cm^2$, so as to ensure its conformal accuracy when treating large tumors. Besides, due to various requirements on shielding and conformity, as well as the technical limitations of the screw, the thickness of the leaves of the multi-leaf collimator ranges from 2.5 mm to 5 mm. That is, the leaf is not only long but also thick, resulting in a large mass of the leaf, which in turn leads to a high requirement on the drive screw, a low movement flexibility of the leaf, and difficulty in increasing the leaf speed, thereby influencing the effect of ray intensity modulation.

Figure 8:
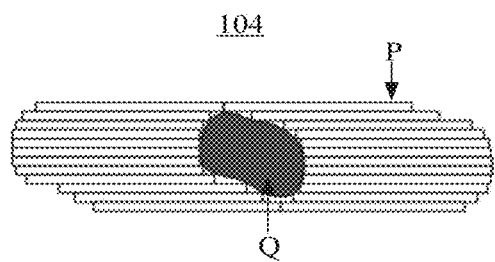
FIG. 8 is a schematic structural diagram of another multi-leaf collimator according to an embodiment of the present disclosure.

FIG. 8 is a schematic structural diagram of another multi-leaf collimator according to an embodiment of the present disclosure. In the present disclosure, as a small multi-leaf collimator can be used to conform to the small field area and the driving requirement is relatively low, leaves of the multi-leaf collimator can be shorter and thinner. For example, the thickness of a leaf in the present disclosure ranges from 2 mm to 2.5 mm. As illustrated in FIG. 8, Q may be a patient's focus which is the same as the focus shown in FIG. 7, the drive screw can control the two sets of leaves to define a conformal region as shown in FIG. 8 (not marked in FIG. 8). As such, a beam emitted from the radiation source may pass through the conformal region and irradiate the focus of a patient to kill tumor cells at the focus, and the regions excess to the focus which have been irradiated is reduced. By comparing FIG. 7 with FIG. 8, it can be seen that in the multi-leaf collimator according to the embodiment of the present disclosure, as its leaves are thinner, the area of the conformal region defined by the leaves and the area of the focus have a relatively small difference and are more similar in shape, and the conformal accuracy is higher, rays emitted from the radiation source can irradiate less healthy tissues of the patient other than the focus area, i.e., rays emitted from the radiation source can irradiate the focus with a higher accuracy.

In the radiation treatment head according to the present disclosure, the length p of a leaf satisfies:

$$\frac{d_1}{2} \cdot \frac{h_1}{h_2} \leq p < d_2 \cdot \frac{h_1}{h_2},$$

where $h_1$ represents a distance between the radiation source and the leaf, $h_2$ represents a distance between the radiation source and the reference plane, $d_1$ represents a minimum length, in a movement direction of the leaf, of a field formed on the reference plane by the beam passing through primary collimation channels after being emitted from the radiation source (i.e., the x direction shown in FIG. 6 or FIG. 9), and $d_2$ represents a maximum length, in a movement direction of the leaf, of a field formed on the reference plane by the beam passing through primary collimation channels after being emitted from the radiation source. The distance $h_2$ between the radiation source and the reference plane may also be referred to as a source to axis distance (SAD).

Figure 9:
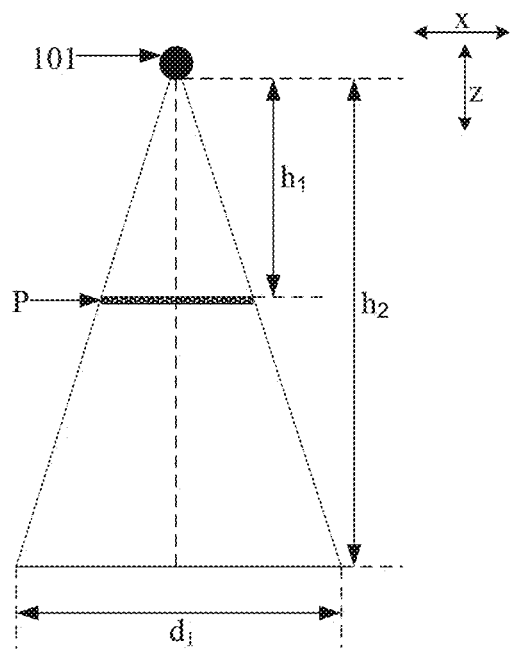
FIG. 9 is a schematic diagram of a radiation source and a second field according to an embodiment of the present disclosure.

For example, when the minimum field formed on the reference plane by the beam emitted from the radiation source is a square with a side length of 28 cm, the side length of the square being the field length on the reference plane in the movement direction of the leaf; and the maximum field formed on the reference plane by the beam emitted from the radiation source is a square with a side length of 40 cm, the side length of the square being the field length on the reference plane in the movement direction of the leaf; then $d_1=28$ cm and $d_2=40$ cm. Referring to FIG. 9, the distance $h_2$ between the radiation source 101 and the reference plane is 100 cm, and the distance $h_1$ between the radiation source and the leaf of the multi-leaf collimator is 40 cm, then the length p of the leaf satisfies:

$$\frac{d_1}{2} \cdot \frac{h_1}{h_2} \leq p < d_2 \cdot \frac{h_1}{h_2}, 14 \times \frac{40}{100} \leq p < 40 \times \frac{40}{100},$$

that is, $5.6 \leq p < 16$. For example, in FIG. 9, when the projection of a set of leaves in the multi-leaf collimator under rays emitted from the radiation source needs to completely cover the minimum field, the length of the leaf in the multi-leaf collimator is $$p = d_1 \cdot \frac{h_1}{h_2} = \frac{28}{100} \times 40 = 11 \cdot 2 \text{ cm}.$$

In the present disclosure, leaves in the multi-leaf collimator may have a length of 11.2 cm. When the multi-leaf collimator is combined with primary collimation channel groups, a minimum field with a field area of 28*28 cm² can be formed. When leaves of the multi-leaf collimator are at a limit position thereof, a maximum field with a field area of 40*40 cm² can be formed, so that it can be applied for treating relatively large tumors. Compared to the multi-leaf collimator in the example shown in FIG. 7, leaves of the multi-leaf collimator of the present disclosure are shorter in length, thinner in thickness and smaller in mass, and thus can be driven by a thinner screw rod. Therefore, in a treatment of a small tumor, a primary collimation channel with a smaller aperture can be used to match the movement of the leaves, so as to reduce a dose received by normal tissues surrounding the tumor, increase a speed of the leaves, optimize a modulation of dose intensity, and improve the treatment effect of small tumors. At the same time, the present disclosure can be applied for the treatment of a relatively large tumor.

In addition, the length p of leaves of the multi-leaf collimator may be $$\frac{d_1}{2} \cdot \frac{h_1}{h_2} \leq p \leq \frac{d_2}{2} \cdot \frac{h_1}{h_2},$$

thus $$14 \times \frac{40}{100} \leq p \leq 20 \times \frac{40}{100},$$

that is $5.6 \leq p \leq 8$. In the multi-leaf collimator, if it only requires that the projection of two sets of leaves under rays emitted from the radiation source completely covers the minimum field, then the length P of leaves of the multi-leaf collimator may be 5.6 cm.

It should be noted that, if the primary collimation channel is in a truncated cone shape and the maximum field formed by the radiation source on the reference plane should be a square with a side length of 40 cm, a circular irradiation range with a diameter of 50 cm needs to be formed when the rays emitted from the radiation source merely passes through the primary collimation channel. When the field is a square with a side length of 40 cm, if the conformal region defined by leaves of the multi-leaf collimator is required to cover all the positions of the field, the length of leaves of the multi-leaf collimator according to the example shown in FIG. 7 needs to be $$\frac{50}{100} \times 40 = 20 \text{ cm},$$

while the length of leaves according to the embodiments of the present disclosure only needs to be 11.2 cm. If the conformal region defined by leaves of the multi-leaf collimator is only required to be located in the middle of a field, the length of leaves of the multi-leaf collimator according to the example shown in FIG. 7 needs to be $$\frac{50}{100} \times 20 = 10 \text{ cm},$$

while the length of leaves according to the embodiments of the present disclosure only needs to be 5.6 cm. Therefore, in the embodiments of the present disclosure, the leaves in the multi-leaf collimator are short in length and light in mass, thus the multi-leaf collimator is light in weight. In addition, since the leaves to be driven by each drive screw is relatively small in weight, the drive screw may drive the leaves in a relatively high speed, which in turn may help to quickly form a conformal region, thereby improving treatment efficiency.

It should be noted that, the above leaf length is only described as an example. In practice, when the leaf length meets the above conditions, there is no need to limit the specific value thereof. For example, when 5.6≤p<16, the value of p may be 7, 8, 10, 14, or the like.

Optionally, each of the first diaphragm and the second diaphragm may include two movable tungsten blocks arranged oppositely. If the secondary collimator assembly only includes the first diaphragm and the multi-leaf collimator, and the movement direction of leaves of the multi-leaf collimator is the x direction, then the movement direction of the two tungsten blocks of the first diaphragm can be the z direction. The first diaphragm is configured to block rays from being transmitted to the field from the region not covered by the leaves, except the conformal region. In addition, when the secondary collimator assembly only includes the first diaphragm and the multi-leaf collimator, the multi-leaf collimator can be located on a side, distal from the radiation source, of the first diaphragm. When the secondary collimator assembly only includes the second diaphragm and the multi-leaf collimator, the multi-leaf collimator may be located on a side, proximal to the radiation source, of the second diaphragm. When the secondary collimator assembly includes the first diaphragm, the second diaphragm and the multi-leaf collimator at the same time, the first diaphragm, the second diaphragm and the multi-leaf collimator may be arranged in sequence along a direction of the primary collimator distal from the radiation source, and the movement direction of the tungsten blocks of the first diaphragm is perpendicular to the movement direction of the tungsten blocks of the second diaphragm, wherein the second diaphragm can be configured to block rays that may pass through a gap between adjacent leaves.

In summary, the radiation treatment head provided by the embodiment of the present disclosure includes a radiation source and a primary collimator. The primary collimator is provided with a plurality of primary collimation channel groups, each of the primary collimation channel groups includes at least one primary collimation channel, and the radiation source and the primary collimator are configured to be movable relative to each other, so that the beam emitted from the radiation source is permissible to pass through any one of the primary collimation channels; and the beam emitted from the radiation source, after passing through primary collimation channels of different primary collimation channel groups, can form fields with different sizes of areas on the reference plane. In this way, the radiation treatment head can form various fields, which improves the flexibility of the radiation treatment head.

Some embodiments of the present disclosure further provide a radiation treatment device including the radiation treatment head as shown in FIG. 1b or FIG. 5. Optionally, the radiation treatment device may further include a circular gantry or a C-arm gantry, on which the radiation treatment head can be arranged.

For example, the radiation treatment device may be a medical accelerator, and the radiation treatment head may be arranged on a support arm of the circular gantry or C-arm gantry. When employed to treat the focus inside the patient, the radiation treatment device is operated to: align the isocenter of the radiation treatment device with the focus; and control the support arm to drive the radiation treatment head to rotate around the isocenter with the isocenter being a center; and treat the focus. Since the radiation treatment head in the radiation treatment device in the embodiments of the present disclosure is light in weight, the support arm can easily drive the radiation treatment head to rotate, and the radiation treatment device can more accurately align its isocenter with the patient focus.

Described above are merely optional embodiments of the present disclosure, and are not intended to limit the present disclosure. Within the spirit and principles of the present disclosure, any modifications, equivalent substitutions, improvements, and the like should fall within the protection scope of the present disclosure.

What is claimed is:

1. A radiation treatment head, comprising:
a radiation source and a primary collimator,
wherein the radiation source is configured to emit a radioactive beam;
wherein the primary collimator is provided with a plurality of primary collimation channel groups; each of the primary collimation channel groups comprises at least one primary collimation channel; and the radiation source and the primary collimator are movable relative to each other, so that the beam emitted from the radiation source is permissible to pass through any one of the primary collimation channels;
wherein the beam emitted from the radiation source, after passing through primary collimation channels of different primary collimation channel groups, forms fields with different sizes of areas on a reference plane;
wherein the radiation treatment head further comprises a secondary collimator assembly, wherein the secondary collimator assembly comprises a multi-leaf collimator (MLC), and the MLC comprises a plurality of leaves in opposite arrangement and movable relative to each other; and
wherein a length p of the leaf of the MLC satisfies the following formula:

$$\frac{d_1}{2} \cdot \frac{h_1}{h_2} \leq p < d_2 \cdot \frac{h_1}{h_2},$$

where $h_1$ represents a distance between the radiation source and the leaf, $h_2$ represents a distance between the radiation source and the reference plane, $d_1$ represents a minimum length, in a movement direction of the leaf, of a field formed on the reference plane by the beam passing through primary collimation channels after being emitted from the radiation source, and $d_2$ represents a maximum length, in a movement direction of the leaf, of a field formed on the reference plane by the beam passing through primary collimation channels after being emitted from the radiation source.

2. The radiation treatment head according to claim 1, wherein the beam emitted from the radiation source, after passing through the respective primary collimation channels in a same primary collimation channel group, forms fields with different characteristic parameters on the reference plane, wherein the characteristic parameters comprise a dose rate parameter or a penumbra parameter of a field.

3. The radiation treatment head according to claim 2, wherein each of the primary collimation channel groups comprises at least two primary collimation channels, in which at least one is provided with a flattening filter, so that the beam, after passing through the at least two primary collimation channels, forms fields with different characteristic parameters of fields on the reference plane.

4. The radiation treatment head according to claim 2, wherein no flattening filter is provided in one of the primary collimation channels in a primary collimation channel group.

5. The radiation treatment head according to claim 1, wherein the secondary collimator assembly further comprises one or two diaphragms; and wherein when the secondary collimator assembly comprises two diaphragms, a movement direction of a first one of the two diaphragms intersects a movement direction of a second one of the two diaphragms.

6. The radiation treatment head according to claim 1, wherein the primary collimator is in a circular shape, and the plurality of primary collimation channels in the primary collimator are distributed in a circumferential array; and
wherein the radiation source and the primary collimator are rotatable relative to each other, so that the beam emitted from the radiation source is permissible to pass through any one of the primary collimation channels.

7. The radiation treatment head according to claim 1, wherein the primary collimator is plate-shaped, and the plurality of primary collimation channels in the primary collimator are distributed in a straight line or in an array.

8. The radiation treatment head according to claim 1, wherein among the fields formed on the reference plane by the beam passing through the primary collimation channels after being emitted from the radiation source, a maximum file area is 40*40 cm², and a minimum file area is 28*28 cm².

9. The radiation treatment head according to claim 1, wherein among the fields formed on the reference plane by the beam passing through the primary collimation channels after being emitted from the radiation source, a maximum file area is 35*35 cm², and a minimum file area is 22*22 cm².

10. A radiation treatment device, comprising:
a couch and a radiation treatment head, wherein the radiation treatment head comprises a radiation source and a primary collimator,
the radiation source is configured to emit a radioactive beam;
the primary collimator is provided with a plurality of primary collimation channel groups; each of the primary collimation channel groups comprises at least one primary collimation channel; and the radiation source and the primary collimator are movable relative to each other, so that the beam emitted from the radiation source is permissible to pass through any one of the primary collimation channels;
the beam emitted from the radiation source, after passing through primary collimation channels of different primary collimation channel groups, forms fields with different sizes of areas on a reference plane;
wherein the radiation treatment head further comprises a secondary collimator assembly, wherein the secondary collimator assembly comprises a multi-leaf collimator (MLC), and the MLC comprises a plurality of leaves in opposite arrangement and movable relative to each other; and
wherein a length p of the leaf of the MLC satisfies the following formula:

$$\frac{d_1}{2} \cdot \frac{h_1}{h_2} \leq p < d_2 \cdot \frac{h_1}{h_2},$$

where $h_1$ represents a distance between the radiation source and the leaf, $h_2$ represents a distance between the radiation source and the reference plane, $d_1$ represents a minimum length, in a movement direction of the leaf, of a field formed on the reference plane by the beam passing through primary collimation channels after being emitted from the radiation source, and $d_2$ represents a maximum length, in a movement direction of the leaf, of a field formed on the reference plane by the beam passing through primary collimation channels after being emitted from the radiation source.

11. The radiation treatment device according to claim 10, wherein the beam emitted from the radiation source, after passing through the respective primary collimation channels in a same primary collimation channel group, forms fields with different characteristic parameters on the reference plane, wherein the characteristic parameters comprise a dose rate parameter or a penumbra parameter of a field.

12. The radiation treatment device according to claim 11, wherein each of the primary collimation channel groups comprises at least two primary collimation channels, in which at least one is provided with a flattening filter, so that the beam, after passing through the at least two primary collimation channels, forms fields with different characteristic parameters of fields on the reference plane.

13. The radiation treatment device according to claim 11, wherein no flattening filter is provided in one of the primary collimation channels in a primary collimation channel group.

14. The radiation treatment device according to claim 10, wherein the secondary collimator assembly further comprises one or two diaphragms; and wherein when the secondary collimator assembly comprises two diaphragms, a movement direction of a first one of the two diaphragms intersects a movement direction of a second one of the two diaphragms.

15. The radiation treatment device according to claim 10, wherein the primary collimator is in a circular shape, and the plurality of primary collimation channels in the primary collimator are distributed in a circumferential array; and
wherein the radiation source and the primary collimator are rotatable relative to each other, so that the beam emitted from the radiation source is permissible to pass through any one of the primary collimation channels.

16. The radiation treatment device according to claim 10, wherein the primary collimator is plate-shaped, and the plurality of primary collimation channels in the primary collimator are distributed in a straight line or in an array.

17. The radiation treatment device according to claim 10, wherein among the fields formed on the reference plane by the beam passing through the primary collimation channels after being emitted from the radiation source, a maximum file area is 40*40 cm², and a minimum file area is 28*28 cm².

18. The radiation treatment device according to claim 10, among the fields formed on the reference plane by the beam passing through the primary collimation channels after being emitted from the radiation source, a maximum file area is 35*35 cm², and a minimum file area is 22*22 cm².

* * * * *